(12) United States Patent
So et al.

(10) Patent No.: US 11,466,977 B2
(45) Date of Patent: Oct. 11, 2022

(54) SUBCUTANEOUS FAT THICKNESS MEASUREMENT BY RAMAN SPECTROSCOPY

(71) Applicant: Massachusetts Institute of Technology, Cambridge, MA (US)

(72) Inventors: Peter T. C. So, Boston, MA (US); Jeon Woong Kang, Melrose, MA (US); Hyung Min Kim, Seoul (KR)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/249,932

(22) Filed: Mar. 18, 2021

(65) Prior Publication Data

US 2021/0356251 A1 Nov. 18, 2021

Related U.S. Application Data

(60) Provisional application No. 63/026,473, filed on May 18, 2020.

(51) Int. Cl.
  *G01B 11/06* (2006.01)
(52) U.S. Cl.
  CPC ................... *G01B 11/06* (2013.01)
(58) Field of Classification Search
  CPC .................................................... G01B 11/06
  USPC ........................................................ 356/301
  See application file for complete search history.

(56) References Cited

U.S. PATENT DOCUMENTS

| 8,130,376 B2 | 3/2012 | Villaumie |
| 10,542,920 B2 | 1/2020 | Sato |
| 10,627,349 B2 | 4/2020 | Han et al. |
| 2009/0033928 A1* | 2/2009 | Azi .................... G01J 3/021 356/301 |

(Continued)

FOREIGN PATENT DOCUMENTS

| CN | 109497964 A * | 3/2019 | ........... A61B 5/0075 |
| WO | 2019183348 A1 | 9/2019 | |

OTHER PUBLICATIONS

Anderson et al., "Raman Spectroscopy Differentiates Each Tissue from the Skin to the Spinal CordA Novel Method for Epidural Needle Placement?." Anesthesiology: The Journal of the American Society of Anesthesiologists 125.4 (2016): 793-804.

(Continued)

*Primary Examiner* — Dominic J Bologna
*Assistant Examiner* — Omar H Nixon
(74) *Attorney, Agent, or Firm* — Smith Baluch LLP

(57) ABSTRACT

Since the fat content of pork is a deciding factor in grading the quality of meat, the use of a noninvasive subcutaneous probe for real-time, in situ monitoring of the fat components is of importance to vendors and other interested parties. Fortunately, in situ, in vivo monitoring of subcutaneous fat can be accomplished with spatially offset Raman spectroscopy (SORS) using a fiber-optic probe. The probe acquires Raman spectra as a function of spatial offset. These spectra are used to determine the relative composition of fat-to-skin. The Raman intensity ratio varies disproportionately depending on the fat content, with variations in slope that are correlated to the thickness of the fat layer. Ordinary least square (OLS) regression using two components indicates that depth-resolved SORS spectra reflect the relative thickness of the fat layer.

21 Claims, 10 Drawing Sheets

(56) References Cited

U.S. PATENT DOCUMENTS

| | | | | |
|---|---|---|---|---|
| 2009/0306521 | A1* | 12/2009 | Ermakov | A61B 5/0075 600/587 |
| 2014/0140594 | A1* | 5/2014 | Mahadevan-Jansen | G06T 7/0012 382/128 |
| 2016/0331238 | A1* | 11/2016 | Kim | A61B 5/0075 |
| 2016/0354015 | A1* | 12/2016 | Zhang | A61B 5/0075 |
| 2017/0205348 | A1* | 7/2017 | Obara | G01N 21/6486 |
| 2017/0303829 | A1* | 10/2017 | Cohen | A61B 5/0075 |
| 2018/0184972 | A1* | 7/2018 | Carmi | A61B 5/4872 |
| 2018/0310827 | A1* | 11/2018 | Yang | A61B 5/0075 |
| 2019/0257759 | A1 | 8/2019 | Han et al. | |
| 2020/0253561 | A1 | 8/2020 | Han et al. | |
| 2020/0305776 | A1 | 10/2020 | Han et al. | |
| 2020/0330069 | A1* | 10/2020 | Ogura | A61B 8/485 |

OTHER PUBLICATIONS

Beganović et al., "Critical review on the utilization of handheld and portable Raman spectrometry in meat science." Foods 8.2 (2019): 49. 18 pages.

Brosnan et al., "Improving quality inspection of food products by computer vision—a review." Journal of food engineering 61.1 (2004): 3-16.

Buschman et al., "Diagnosis of human coronary atherosclerosis by morphology-based Raman spectroscopy." Cardiovascular Pathology 10.2 (2001): 59-68.

Chan et al., "Label-free separation of human embryonic stem cells and their cardiac derivatives using Raman spectroscopy." Analytical chemistry 81.4 (2009): 1324-1331.

Conti et al., "Determination of thickness of thin turbid R-10 References painted over-layers using micro-scale spatially offset raman spectroscopy." Philosophical Transactions of the Royal Society A: Mathematical, Physical and Engineering Sciences 374.2082 (2016): 20160049. 8 pages.

Fowler et al., "Investigation of chemical composition of meat using spatially off-set Raman spectroscopy." Analyst 144.8 (2019): 2618-2627.

Frank et al., "A statistical view of some chemometrics regression tools." Technometrics 35.2 (1993): 109-135.

Hewitt et al., "Accurate assessment of liver steatosis in animal models using a high throughput Raman fiber optic probe." Analyst 140.19 (2015): 6602-6609.

Hitchens et al., "Prevalence and risk factors for overweight horses at premises in Sweden assessed using official animal welfare control data." Acta Veterinaria Scandinavica 58.1 (2016): 31-35.

International Search Report and Written Opinion in International Patent Application No. PCT/US2021/070289 dated May 18, 2021, 9 pages.

Köşüş et al., "Relation between abdominal subcutaneous fat tissue thickness and inflammatory markers during pregnancy." Archives of Medical Science: AMS 10.4 (2014): 739. 7 pages.

Kouba et al., "A review of the factors influencing the development of intermuscular adipose tissue in the growing pig." Meat Science 88.2 (2011): 213-220.

Krafft et al., "Mapping of single cells by near infrared Raman microspectroscopy." Vibrational Spectroscopy 32.1 (2003): 75-83.

Lee et al., "Abdominal subcutaneous fat thickness measured by ultrasonography correlates with hyperlipidemia and steatohepatitis in obese children." Pediatric Gastroenterology, Hepatology & Nutrition 18.2 (2015): 108-114.

Lonergan et al., The science of animal growth and meat technology. Academic Press, 2018. 280 pages.

Lyndgaard et al., "Depth profiling of porcine adipose tissue by Raman spectroscopy." Journal of Raman Spectroscopy 43.4 (2012): 482-489.

MacLeod et al., "Prediction of sublayer depth in turbid media using spatially offset Raman spectroscopy." Analytical Chemistry 80.21 (2008): 8146-8152.

Matousek et al., "Numerical simulations of subsurface probing in diffusely scattering media using spatially offset Raman spectroscopy." Applied Spectroscopy 59.12 (2005): 1485-1492.

Meksiarun et al., "Analysis of the effects of dietary fat on body and skin lipids of hamsters by Raman spectroscopy." Analyst 140.12 (2015): 4238-4244.

Personalized Belly Fat Solution Bello. Accessed at http://olive-hc.com/contents.php?con_id=bello_eng on Jul. 2, 2021. 5 pages.

Scholz et al., "Non-invasive methods for the determination of body and carcass composition in livestock: dual-energy X-ray absorptiometry, computed tomography, magnetic resonance imaging and ultrasound: invited review." Animal 9.7 (2015): 1250-1264.

Song et al., "Hyperspectral Raman line mapping as an effective tool to monitor the coating thickness of pharmaceutical tablets." Analytical Chemistry 91.9 (2019): 5810-5816.

Stevens et al., "Developing fibre optic Raman probes for applications in clinical spectroscopy." Chemical Society Reviews 45.7 (2016): 1919-1934.

Stolen et al., "Development of the stimulated Raman spectrum in single-mode silica fibers." JOSA B 1.4 (1984): 652-657.

Störchle et al., "Measurement of mean subcutaneous fat thickness: eight standardised ultrasound sites compared to 216 randomly selected sites." Scientific Reports 8.1 (2018): 1-12.

Su et al., "Depth-sensitive Raman spectroscopy for skin wound evaluation in rodents." Biomedical Optics Express 10.12 (2019): 6114-6128.

Tao et al., "Recent advances in rapid and nondestructive determination of fat content and fatty acids composition of muscle foods." Critical Reviews in Food Science and Nutrition 58.9 (2018): 1565-1593.

VandenAbeele et al., "Development of a fiber-optics microspatially offset Raman spectroscopy sensor for probing layered materials." Analytical Chemistry 89.17 (2017): 9218-9223.

Weissleder, "A clearer vision for in vivo imaging." Nature Biotechnology 19.4 (2001): 316-317.

Wood et al., "Effects of breed, diet and muscle on fat deposition and eating quality in pigs." Meat Science 67.4 (2004): 651-667.

* cited by examiner

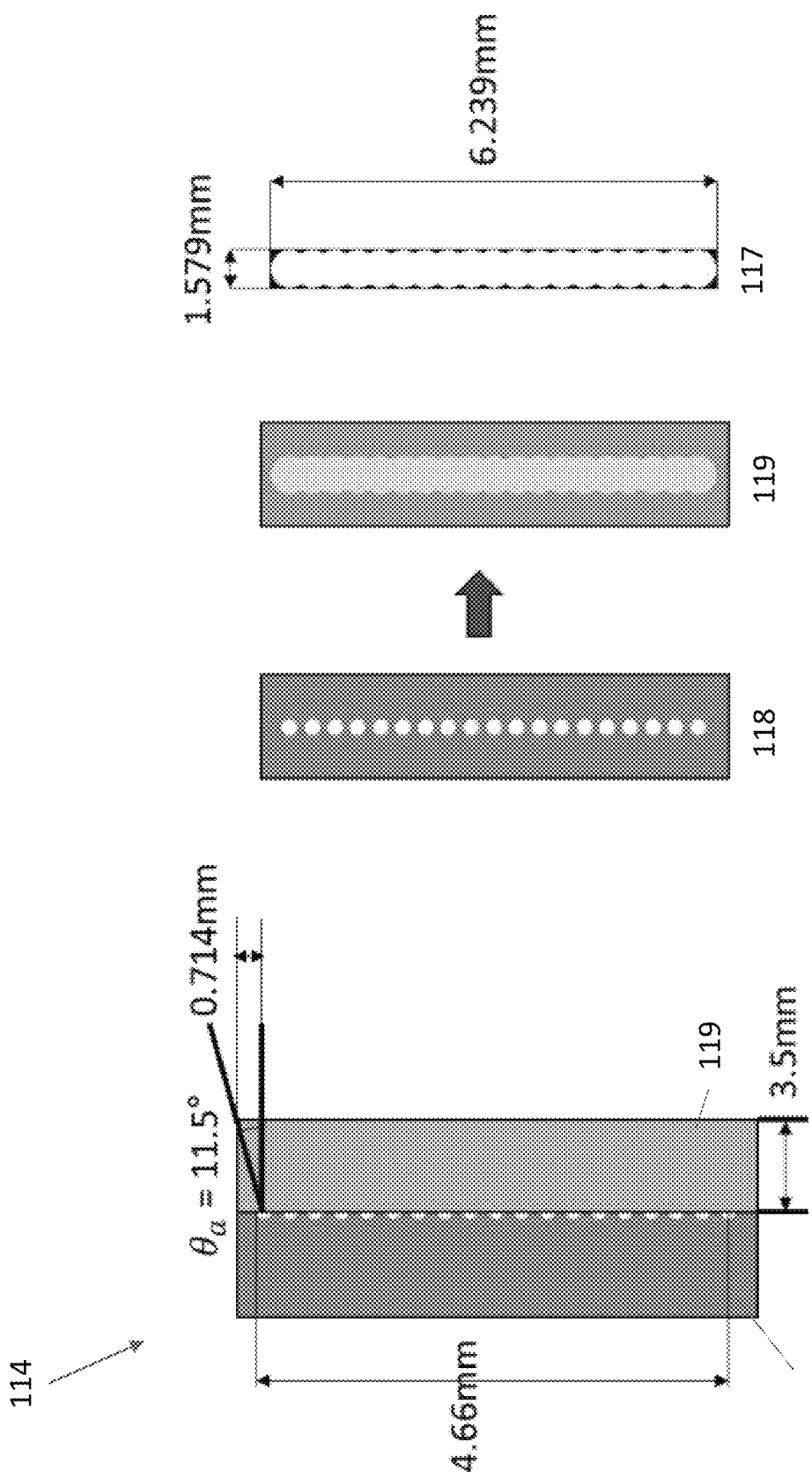

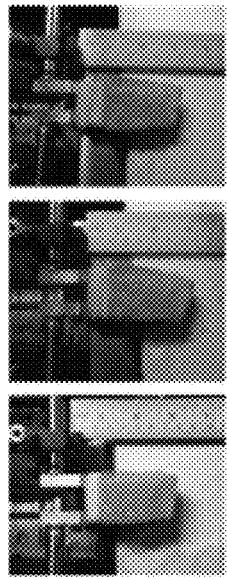
FIG. 3A
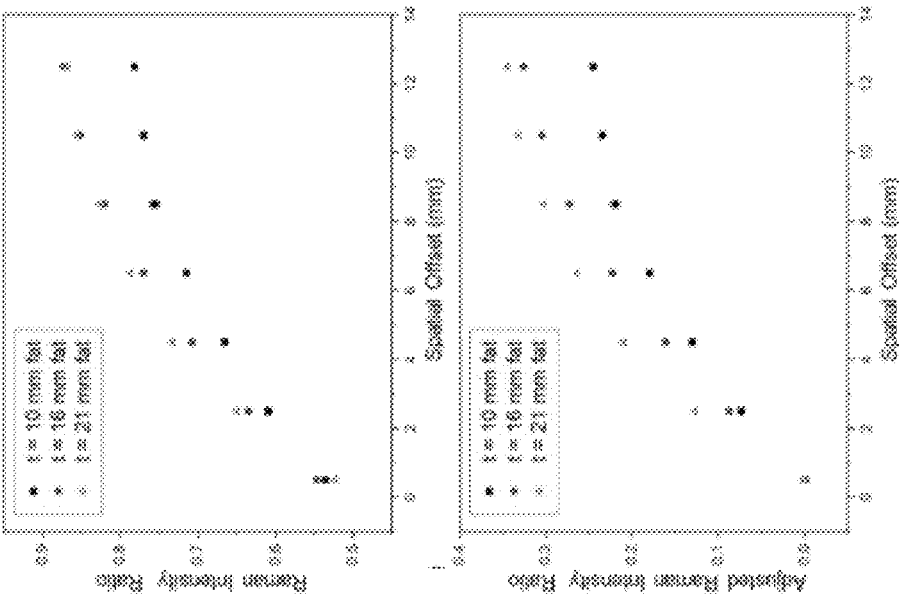
FIG. 3B
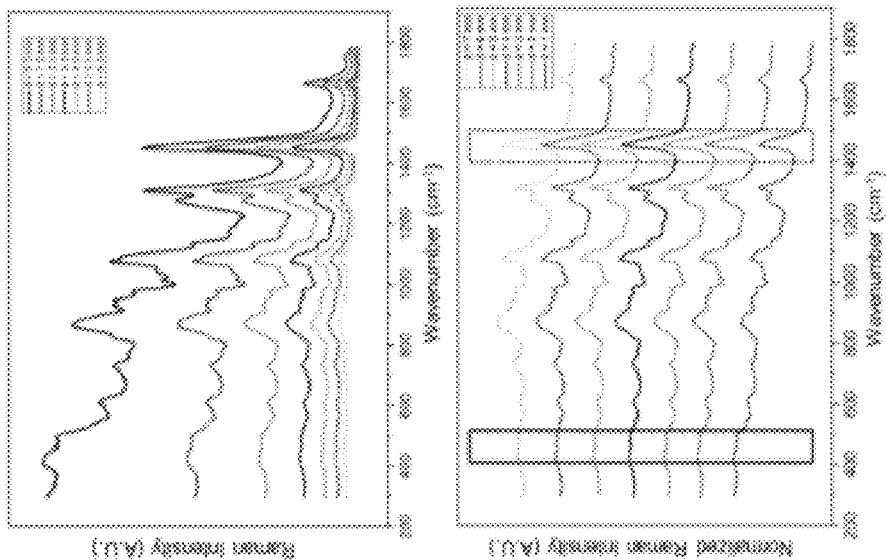
FIG. 3C
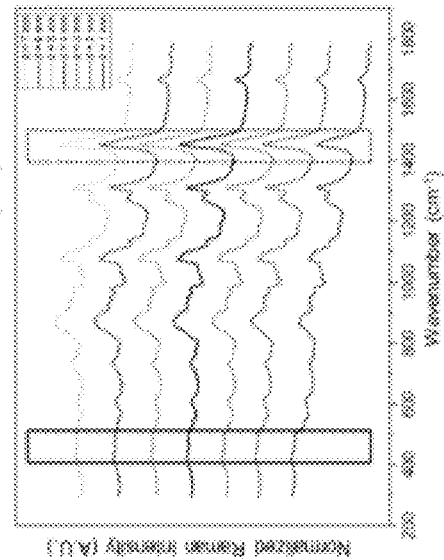
FIG. 3D
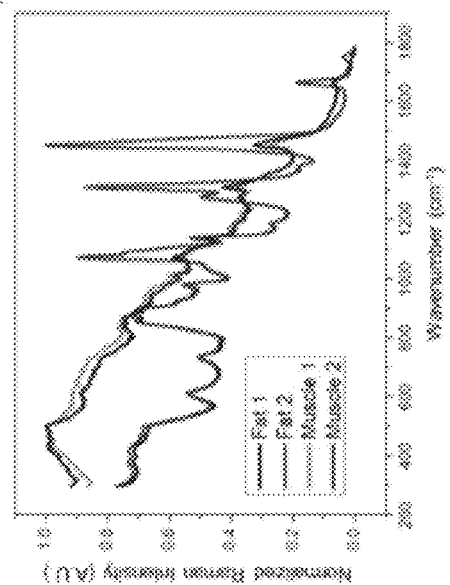
FIG. 3E
FIG. 3F

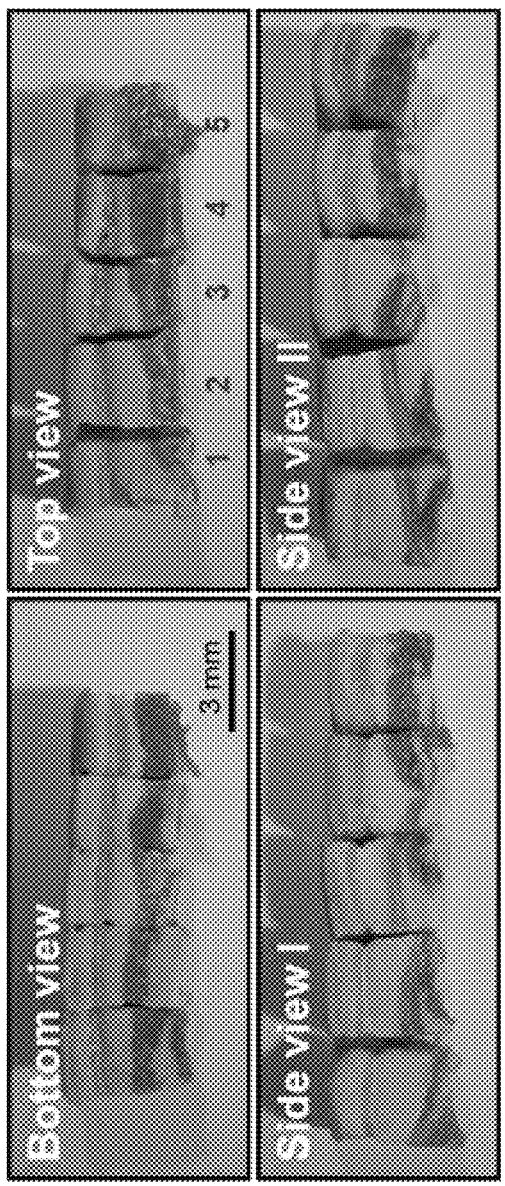
*FIG. 4A*
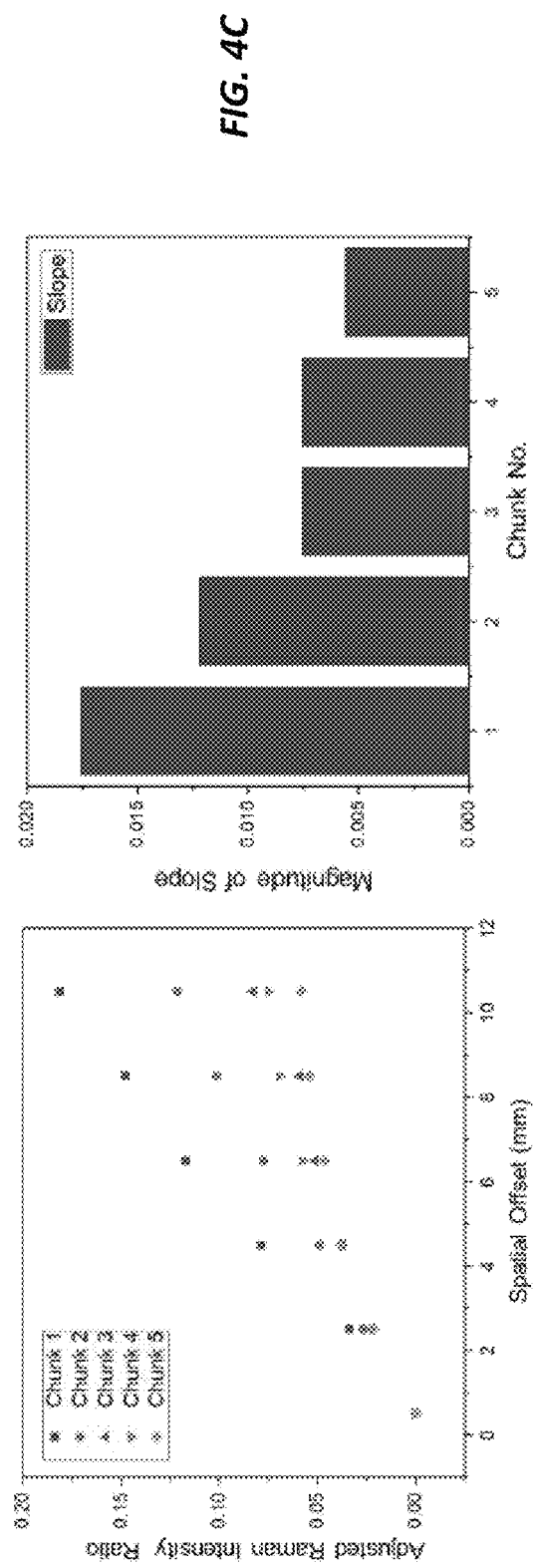
*FIG. 4B*
*FIG. 4C*

SUBCUTANEOUS FAT THICKNESS MEASUREMENT BY RAMAN SPECTROSCOPY

CROSS-REFERENCE TO RELATED APPLICATION(S)

This application claims the priority benefit, under 35 U.S.C. 119(e), of U.S. Application No. 63/026,473, filed May 18, 2020, which is incorporated by reference herein in its entirety.

GOVERNMENT SUPPORT

This invention was made with Government support under Grant No. P41 EB015871 awarded by the National Institutes of Health (NIH). The Government has certain rights in the invention.

BACKGROUND

The quality grade of pork products is determined by numerous factors, including color, exudation, and the extent of marbling. The thickness of subcutaneous fat, especially backfat, is a typical marker used in the carcass grading system. For pork, subcutaneous fat accounts for most of the dissected pork belly. Since the fat content affects the use and grade of the meat, measuring the fat thickness of carcasses or live stocks is of utmost importance.

Typically, fat layers are distributed under the skin (subcutaneous), in the middle of and between layers of muscle (intramuscular and intermuscular, respectively), and within the abdominal cavity (visceral). Of these classifications, subcutaneous and intermuscular fat account for 80%-95% of the total body fat of a pig. In the livestock industry, the body composition is monitored by measuring the backfat thickness and the loin muscle depth to determine the lean meat content and grading, and pigs are slaughtered at different times, depending on the purpose of their future consumption. Visual evaluation, computer vision, backfat probes, and ultrasound technology are typically used to measure the fat and lean contents of both carcasses and livestock. Alternative methods of evaluation, such as dual-energy X-ray absorptiometry, computed tomography, magnetic resonance imaging electronic meat-measuring equipment, and total body electrical conductivity, are often employed as a complement to the aforementioned techniques for body/carcass grading.

The method of measuring subcutaneous fat in any given situation depends on a variety of factors as each technique has its own advantages and drawbacks. For example, despite its reputation for being noninvasive and rapid, visual evaluation is limited in its availability to the general public as this evaluation technique can only be conducted by trained experts. A backfat probe provides accurate information about the backfat thickness and the loin eye area at a low cost, but an incision must be made into the animal's skin, which can have an undesired outcome on the quality of the meat and the safety of the animal. Ultrasonic evaluation is the most reliable method used to measure fat content, in particular fat thickness, of live animals and is a popular choice in the livestock industry. However, the readings obtained are heavily influenced by the animal's water contents at the time of measurement as well as the prevailing temperature conditions. Given the numerous shortcomings of the techniques mentioned above, it is unsurprising that a new real-time, noninvasive method, which is robust against fluctuations caused by changing water content and temperature variations while still offering high-resolution results, is urgently desired.

SUMMARY

Near-infrared (NIR) Raman spectroscopy can be used for real-time, noninvasive measurements of subcutaneous fat. Raman spectroscopy measurements are robust against fluctuations caused by changing water content and temperature variations while still offering high-resolution results. And unlike other subcutaneous fat measurement techniques, they can also be used to measure both chemical and physical information about the fat content in a single measurement because biological tissues are relatively transparent for across the NIR wavelength window of 650 nm to 900 nm.

NIR Raman spectroscopy is broadly used for the noninvasive analysis of the chemical composition of beef and pork. Moreover, Raman spectroscopy can be used for assessing fat firmness and tenderness, in addition to evaluating the animal's fat and fatty acid content. In Raman measurements, the type and quantity of the fatty acid can be readily determined based on characteristic vibrational features since saturated and unsaturated fatty acids show different spectral patterns in the $CH_2/CH_3$ vibrational window and the number and chemical bonding of carbon atoms present in each molecule influences the Raman fingerprint of the fatty acid.

In vivo and ex vivo fat analyses can be accomplished using a fiber-optic Raman probe for depth-resolved, spatially offset Raman spectroscopy (SORS). In SORS, spectral analysis of the deeper layers is conducted by adjusting the distance or offset between the incidence of the laser and the Raman detection. This multi-offset SORS technique can be used to measure the thickness of a subcutaneous fat layer by first making Raman measurements at different offsets. Analyzing the Raman spectra provides information about the chemical components of swine tissue samples. These chemical components can be used to identify Raman returns the different layers (skin, fat, muscle) and to determine the thickness of the fat layer noninvasively.

The slope of the Raman signal intensity fluctuates in proportion to the fat thickness, making it possible to estimate the local fat distribution from an ordinary least squares (OLS) analysis. The OLS analysis acts as a two-component model to identify the relative ratio of muscle and fat components. For quantitative analysis, the acquired Raman spectra from the tissue specimens are decomposed as a summation of two basis components: fat and muscle (non-fat). For the OLS analysis, nonnegative linear least-squares curve fitting equations are solved. Each acquired spectrum can be represented by two fitting coefficients representing the relative amounts of the fat and muscle basis components.

A method of measuring a subcutaneous fat layer in a mammal may include illuminating a first spot on the skin of the mammal with a Raman pump beam. The Raman pump beam excites a Raman emission from the subcutaneous fat layer. This Raman is detected at a second spot on the skin of the mammal. The thickness of the subcutaneous fat layer can be estimated based on the Raman emission and a distance between the first spot and the second spot, which can be about 0.5 mm to about 20.0 mm. In some cases, the Raman emission is first Raman emission, and the method further comprises detecting a second Raman emission at a third spot on the skin of the mammal and using this second Raman emission and a distance between the first spot and the third spot to estimate the thickness of the subcutaneous fat layer. For instance, estimating the thickness of the subcutaneous fat layer may include determining Raman spectra of the first Raman emission and the second Raman emission, determining Raman intensity ratios (ratios of the Raman intensity from fat to the Raman intensity from a reference, such as the optical fiber that guides the Raman pump beam) for the second spot and the third spot based on the Raman spectra, and estimating a variation of the Raman intensity ratio with distance from the first spot based on the Raman intensity ratios.

Another method of measuring a subcutaneous fat layer in a mammal includes illuminating a first spot on the skin of the mammal with a Raman pump beam. This Raman pump beam excites a Raman emission from the subcutaneous fat layer. A detector measures a variation in amplitude of a spectral component of the Raman emission associated with the subcutaneous fat layer as a function of distance from the first spot (e.g., over 2-5 measurements, each at a different distance). And a processor estimates a thickness of the subcutaneous fat layer based on the variation in amplitude of the spectral component.

A subcutaneous fat layer can be measured in a mammal using a system that includes a laser, excitation optical fibers, collection optical fibers, detector (e.g., a spectrometer or photodetectors with respective bandpass filters), and processor. In operation, the laser emits a Raman pump beam, which the excitation optical fibers guide from the laser to a first spot on the skin of the mammal. The distal ends of the excitation optical fibers are arranged in a first array and illuminate the first spot with the Raman pump beam, which excites a Raman emission from the subcutaneous fat layer. The collection optical fibers have distal ends arranged in a second array to detect the Raman emission at a second spot on the mammal's skin. The detector, which is in optical communication with the collection optical fibers, measures an amplitude of a spectral component of the Raman emission associated with the subcutaneous fat layer. And the processor, which is operably coupled to the detector, estimates a thickness of the subcutaneous fat layer based on the variation in amplitude of the spectral component and a distance between the first spot and the second spot.

The processor can estimate the thickness of the subcutaneous fat layer by determining Raman intensity ratios for the second spot and the third spot based on peaks in Raman spectra of the first Raman emission and the second Raman emission, then estimating a variation of the Raman intensity ratio with distance from the first spot based on the Raman intensity ratios. To determine the Raman intensity ratios, the processor may determine an area under a peak associated with the subcutaneous fat layer at about 1450 cm-1 and an area under a reference peak at about 450 cm-1. It may also determine a slope of the variation of the Raman intensity ratio with distance from the first spots.

The system may also include a first ferrule to hold the distal ends of the excitation optical fibers against the mammal's skin at the first spot and a second ferrule, which is moveable with respect to the first ferrule, to hold the distal ends of the collection optical fibers against the mammal's skin at the second spot. Or the system may include a ferrule to hold the distal ends of the excitation and collection optical fibers against the mammal's skin at the first and second spots, respectively. In this case, the system may include additional collection optical fibers, having distal ends arranged in a third array and held in place by the ferrule, to detect the Raman emission at a third spot on the mammal's skin. The distance between the first spot and the second spot may be a first distance (e.g., between 0.5 mm and 5.0 mm), and the third spot separated from the first spot by a second distance greater than the first distance (e.g., between 5 mm and 20 mm).

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

Figure 1A:
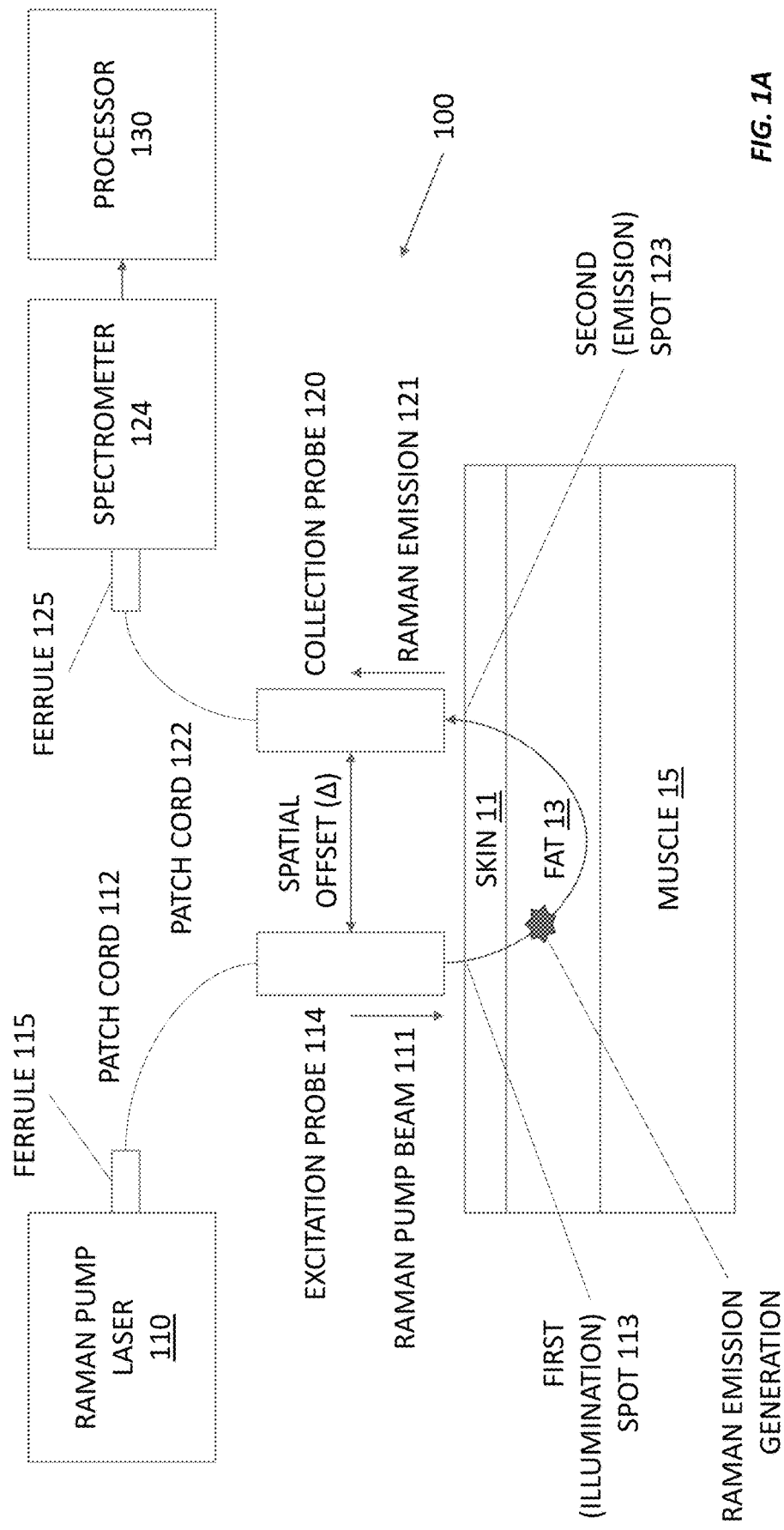
FIG. 1A illustrates a system for subcutaneous fat thickness measurement by Raman spectroscopy with fiber-optic probes for light delivery from a laser (excitation) and a Raman photon delivery to a spectrometer (collection) for in situ fat analysis.
Figures 1B, 1C:
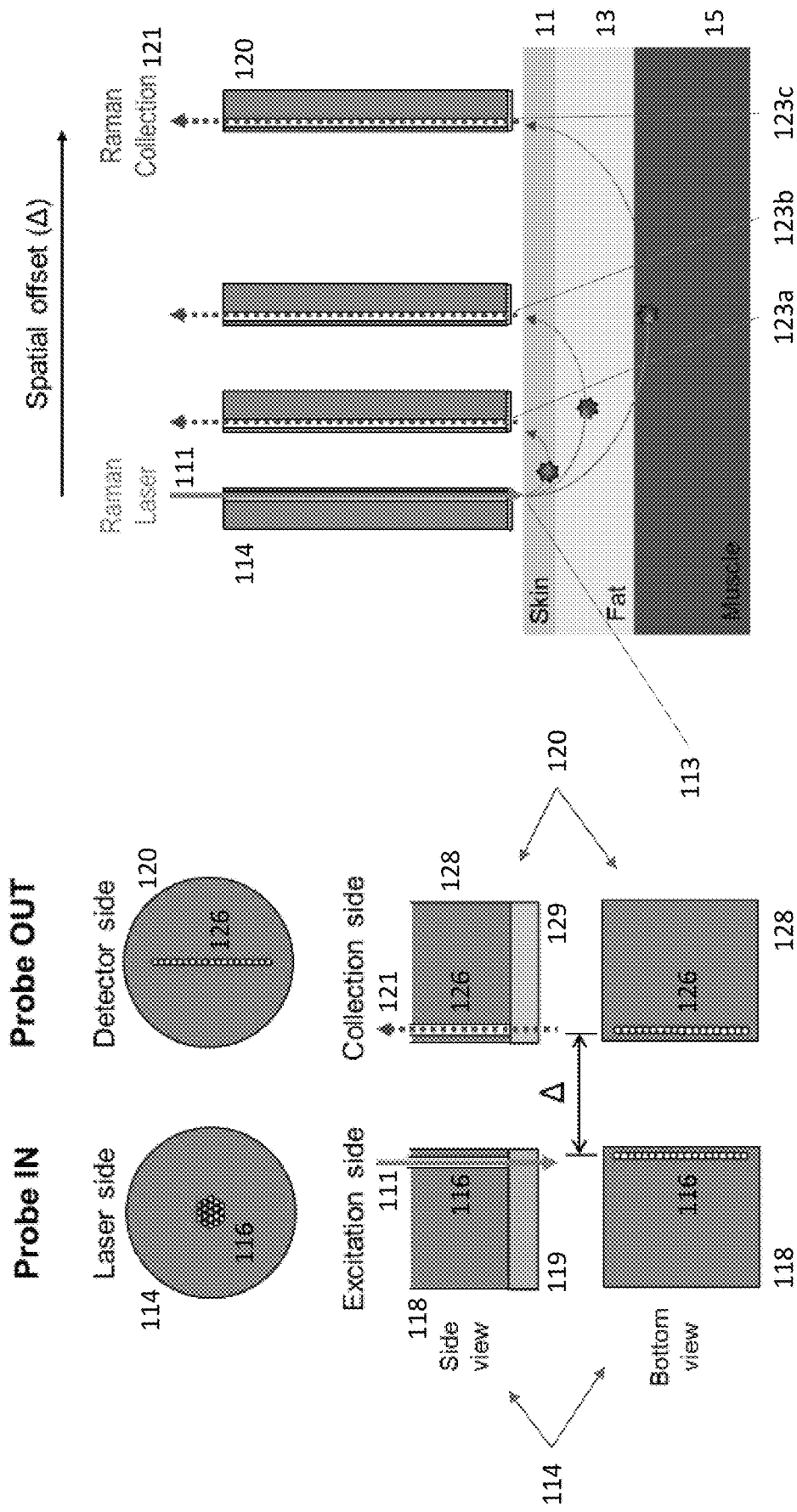
FIG. 1B shows side and bottom views of the proximal ferrules and distal fiber-optic probes of FIG. 1A. The ends of excitation and collection fiber-optic probes are terminated with laser line and long-pass filters, respectively.
FIG. 1C illustrates spatial offset Raman spectroscopy (SORS) using the fiber-optic probes of FIG. 1B.
Figure 1E:
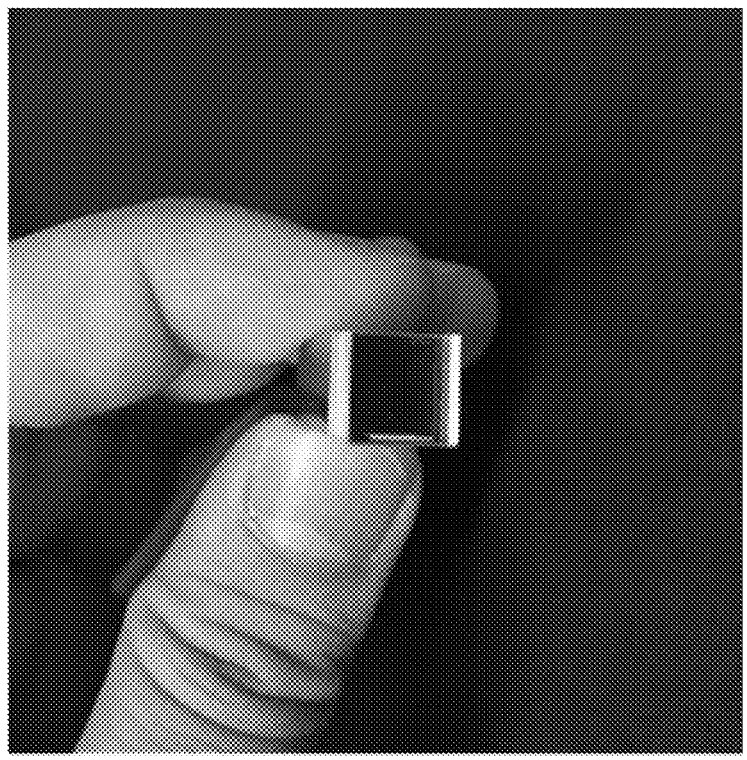
Figure 1D:
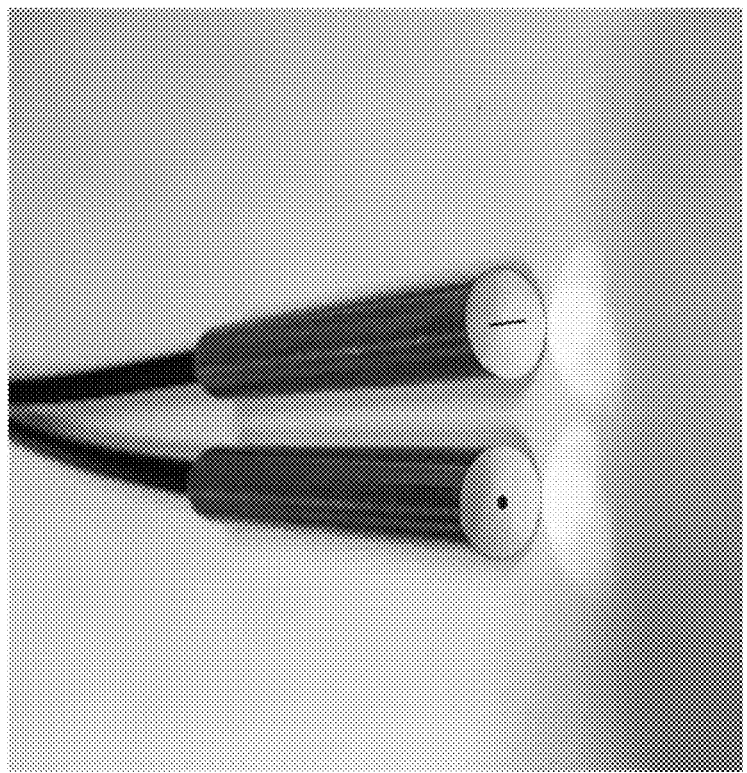

FIG. 1D is a photograph of the ends of the proximal excitation (left) and collection (right) ferrules coupled to the laser and spectrometer, respectively. Each ferrule is cylindrical and has an outer diameter of 10 mm diameter and includes a bundle of 19 fibers, each of which has a 200 µm core (NA=0.22). The diameter of the active area on the excitation ferrule is 1.54 mm.

FIG. 1E is a photograph of an excitation/collection fiber-optic probe covered with an optical filter. The size of probe is 11 mm×10 mm. The dimensions of the linear fiber array on the detection side are 4.66 mm (H)×0.245 mm (W).

FIG. 1F is a schematic of the linear fiber array as viewed from the side.

FIG. 1G is a schematic of the fiber array viewed from the front and enlarged illumination area of the incident laser passing through the filter.

Figure 2:
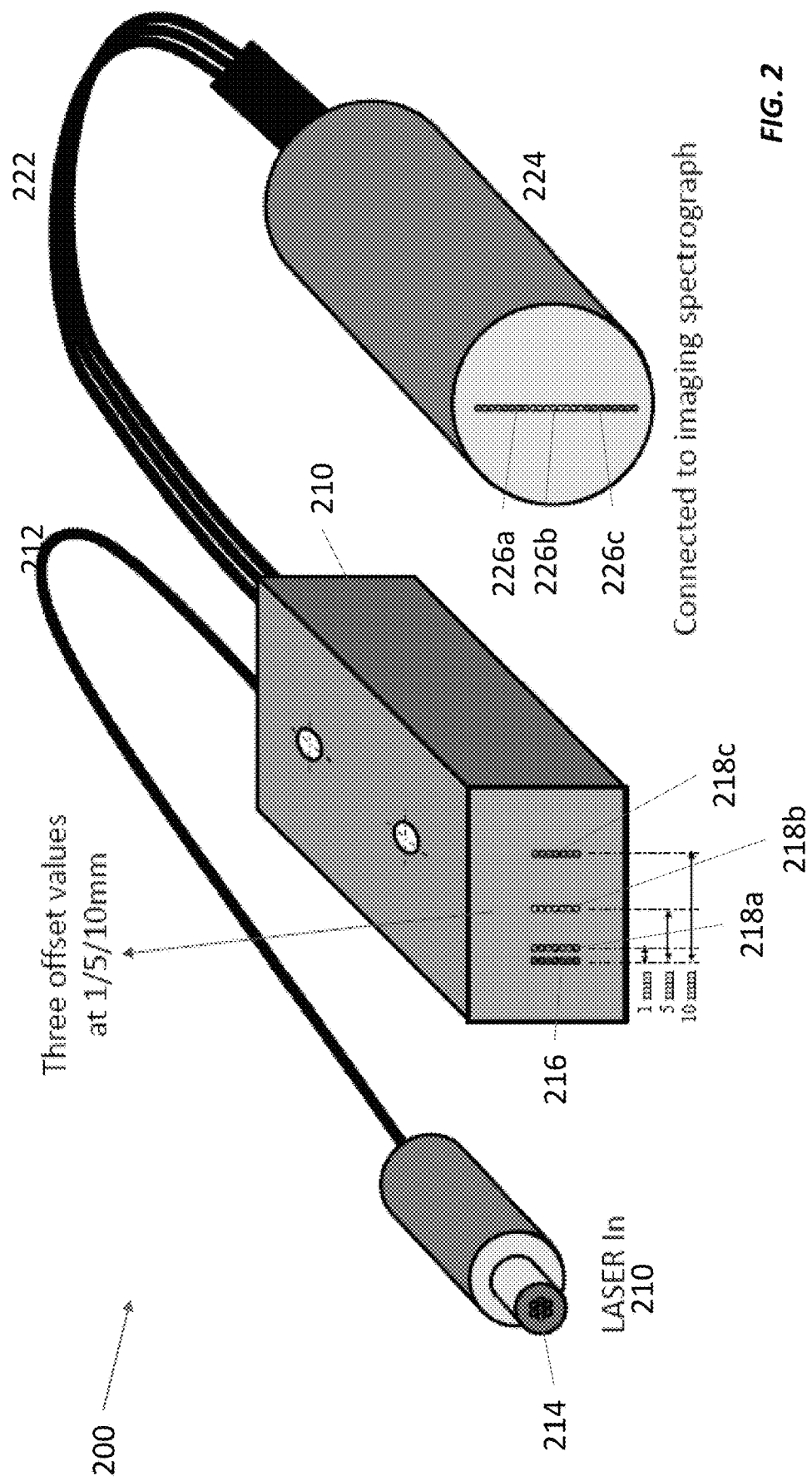

FIG. 2 illustrates a portable Raman spectroscopy probe with an integrated excitation/collection probe for subcutaneous fat measurements.

FIG. 3A illustrates the fat-muscle bilayer model system used for SORS measurements with the fiber-optic probes in FIGS. 1B and 1C. The thicknesses of fat (including skin) in the three pieces are 10, 16, and 20 mm.

FIG. 3B shows Raman spectra of fat and muscle components of the pork tissue sample.

FIG. 3C shows SORS spectra of the pork tissue sample as a function of spatial offset.

FIG. 3D shows the SORS spectra of FIG. 3C normalized using the standard normal variate (SNV), with the designated Raman signature of fat (dashed rectangle) and the background (straight).

FIG. 3E shows the original Raman intensity ratio as a function of offset.

FIG. 3F shows the offset-zeroed Raman intensity ratio as a function of offset.

FIG. 4A is a photograph of a piece of pork purchased from a local grocery store and chopped into five chunks.

FIG. 4B is plot of the measured Raman intensity ratio ($I_{Fat}/I_{Ref}$) as a function of spatial offset for the five pork chunks in FIG. 4A.

FIG. 4C is a plot of the slope constant relative to the pork chunk number.

Figure 5B:
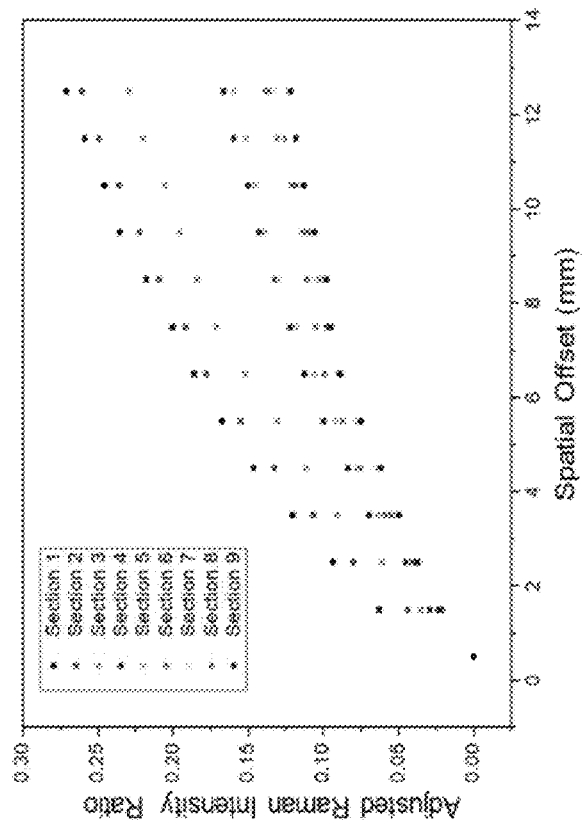
Figure 5A:
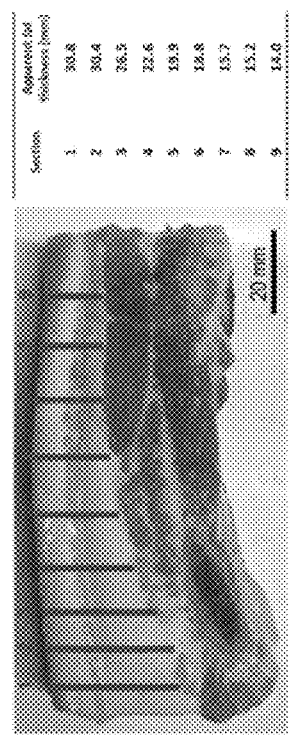

FIG. 5A is an annotated photograph of a pork sample used for SORS analysis with arrows indicating the spatial offsets.

FIG. 5B is a plot of the zeroed Raman intensity ratio as a function of spatial offset for SORS measurements of the pork sample in FIG. 5A.

Figure 5C:
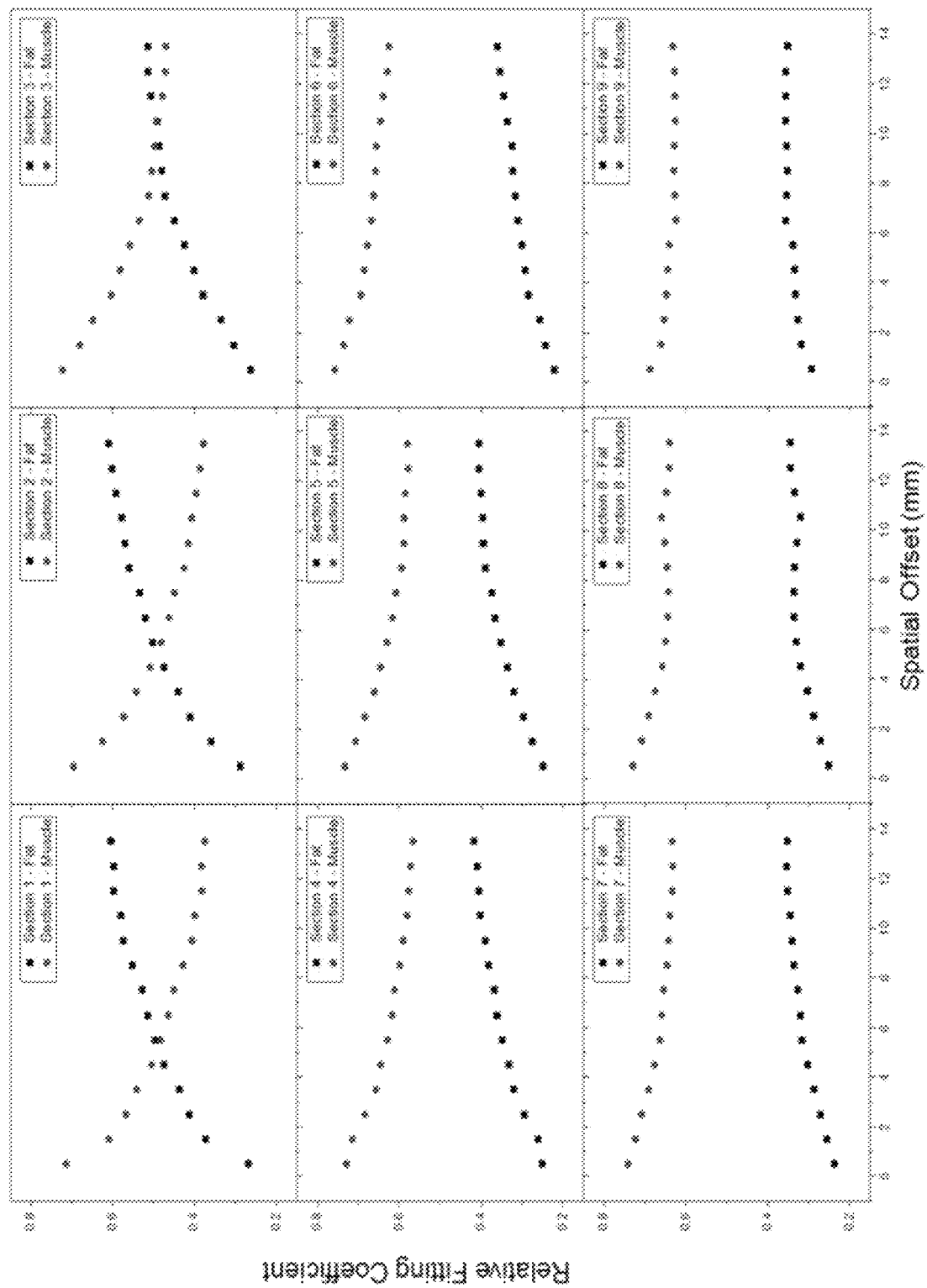

FIG. 5C is a plot of ordinary least square (OLS) regression results for the nine sections of the pork sample in FIG. 5A, representing the composition of the fat and muscle components.

Figure 5D:
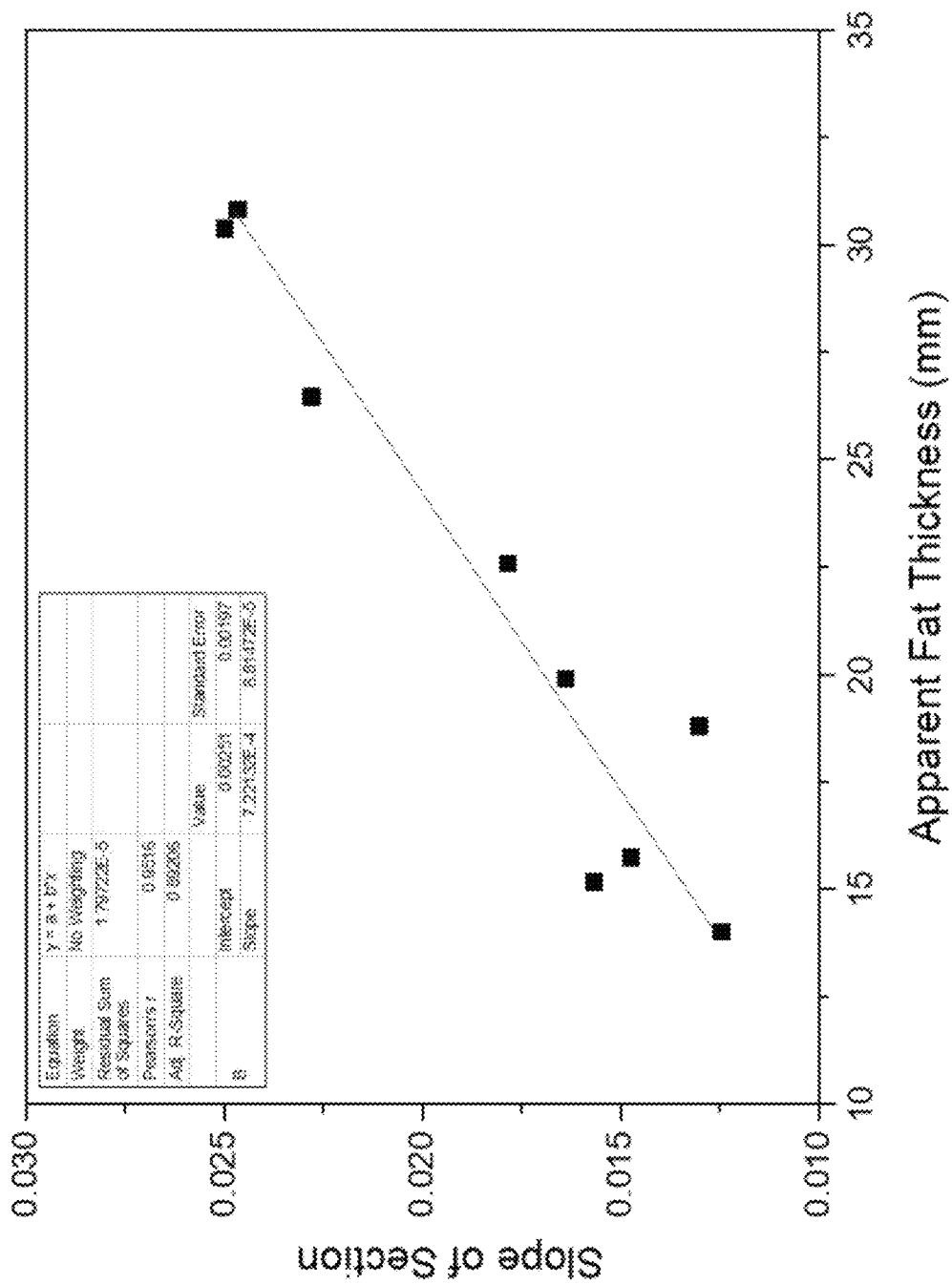

FIG. 5D is a plot of the slope of each section of the pork in FIG. 5A as a function of the apparent thickness of the pork.

DETAILED DESCRIPTION

FIGS. 1A-1G illustrate spatial-offset Raman spectroscopy (SORS) measurements of subcutaneous fat thickness and composition in humans, swine, and other mammals. FIG. 1A shows a complete SORS system 100 being used to measure the thickness and composition of a layer of fat 13 sandwiched between layers of skin 11 and muscle 13. The measurements are made through the layer of skin 11 and can be made in vivo or ex vivo.

The SORS system 100 includes a Raman pump laser 110 (e.g., a diode laser) that emits a continuous-wave Raman pump beam 111 at a wavelength (e.g., 785 nm or 830 nm) and power level (e.g., 10 mW) selected to stimulate Raman emission from the fat 13. The Raman pump laser 110 is detachably connected to the proximal end of an optical fiber patch cord 112 via a ferrule 115 or another suitable connector. The distal end of the optical fiber patch cord terminates in an excitation probe 114 that can be held flush against (i.e., in direct contact with) or just above the surface of the skin 11. The optical fiber patch cord 112 includes one or more multimode optical fibers that guide the Raman pump beam 111 from the Raman pump laser 110 to a first (excitation) spot 115 on the surface of the skin 11. At least some of the Raman pump photons in the Raman pump beam 111 propagate along ballistic paths through the skin 11 and into the layer of fat 13, where they generate Raman photons through nonlinear interactions in and with the fat 13. These Raman photons scatter isotropically within the layer of fat 13, with at least some Raman pump photons following paths to a second (emission) spot 123 on the surface of the skin 11. These Raman pump photons exit the skin 11 as a Raman emission 121 whose amplitude and spectrum contain information about the size, location, and composition of the layer of fat 13. This information depends in part on an adjustable spatial offset A between the first spot 113 and the second spot 123 as discussed below.

The SORS system 100 also includes a collection probe 120 that can be positioned in direct contact with or just above the second spot 123. This collection probe 120 is connected to and couples the Raman emission 121 into the distal end of another optical fiber patch cord 122, which includes one or more multimode optical fibers that guide the Raman photons to a spectrometer 124 or other suitable detector at the proximal end of the optical fiber patch cord 122. The proximal end of the optical fiber patch cord 122 can be detachably coupled to the spectrometer 124 with a ferrule 125 as shown in FIG. 1A or fixed to the spectrometer 124. The spectrometer 124 measures the amplitude spectrum of the Raman emission 121 collected by the collection probe 120. A processor 130 coupled to the spectrometer 124 uses this Raman spectrum and the spatial offset to estimate the thickness and composition of the fat layer 13 as explained below.

Alternatively, the spectrometer 124 can be replaced by a set of photodetectors and bandpass filters, where photodetector and bandpass filter monitors a different spectral bin. For example, the collection probe 120 might have two photodetectors, each with a different bandpass filter, to monitor light in two spectral bins—a reference spectral bin at about 450 $cm^{-1}$ and a fat spectral bin at about 1450 $cm^{-1}$ for calculating the Raman intensity ratio as described below. In this example, the reference bandpass filter has a passband centered at about 450 $cm^{-1}$ and a bandwidth of about 40-50 $cm^{-1}$, and the fat bandpass filter has a passband centered at about 450 $cm^{-1}$ and a bandwidth of about 40-50 $cm^{-1}$.

FIG. 1B shows the ferrules 115 and 125 and fiber-optic probes 114 and 120 configured to acquire offset-adjustable SORS spectra in greater detail. The left-hand column shows the ferrule 115 and probe 114 on the excitation side (Probe IN), and the right-hand column shows the ferrule 125 and probe 120 on the collection side (Probe OUT). The top row shows the ends of the ferrules 115 and 125, the middle row shows profile cross sections of the probes 114 and 120, and the bottom row shows the ends of the probes 114 and 120.

As shown in FIG. 1A, the excitation ferrule 115, patch cord 112, and probe 114 convey the Raman pump beam 111, or excitation beam, from the laser 110 to the first spot 113 on the surface of skin 11. The ferrule 115, patch cord 112, and probe 114 includes a bundle of 19 fibers 116 (Φcore=200 μm) that are arranged in a circle at the proximal end (top left in FIG. 1B and left in FIG. 1D), also called the laser side, that couples to the laser 110 and receives the excitation beam 111 from the laser 110. The fibers 116 are arranged in a linear array and held in place with a square metal ferrule 118 at the distal end of the excitation probe 114 (bottom left in FIG. 1B and FIG. 1E). This square metal ferrule 118 can be place directly against or just above the tissue. A laser line filter 119 (e.g., Semrock, Rochester, USA) affixed to the output face of square ferrule 118 transmits the Raman pump beam 111 and blocks background signals emitted from the delivery fibers 116.

The collection probe 120, patch cord 122, and ferrule 125 collect and convey the Raman light 121 from the tissue to the spectrometer 124 (FIG. 1A). They include a bundle of 19 fibers 126 arranged linearly at both ends. The collection ferrule 125 (top right in FIG. 1B and right in FIG. 1D), which is at the proximal or detector side, has a cylindrical housing and mates or couples to the spectrometer 124. The fibers 126 in the collection probe 120 (bottom right in FIG. 1B and FIG. 1E) are arranged in a linear array at the distal end or collection or skin side. The fibers are held in place by a square metal ferrule 128 that can be placed directly against the tissue. A long-pass filter 129 (e.g., Semrock, Rochester, USA) affixed to the face of the square metal ferrule 128 transmits the Raman emission 121 while simultaneously blocking any Rayleigh pump photons 111 scattered from the sample. A typical long-pass filter 129 may have an optical density (OD) of about 5-6 and transmit more than 90% of the Raman emission 121.

Other examples of excitation optics in a SORS system may include different numbers of fibers (e.g., 20, 30, 40, or 50 fibers) arranged in arrays of other shapes, including square, rectangular, and hexagonal arrays, at the proximal and distal ends. As in FIG. 1B, the fibers can be arranged in arrays of different shapes at the proximal and distal ends (e.g., circular or hexagonal at the proximal/laser side and linear/square at the distal/skin side). Similarly, other examples of collection optics in a SORS system may include different numbers of fibers (e.g., 20, 30, 40, or 50 fibers) arranged in arrays of other shapes, including square, rectangular, and hexagonal arrays, at the proximal and distal ends. As in FIG. 1B, the fibers can be arranged in arrays of different shapes at the proximal and distal ends (e.g., circular or hexagonal at the proximal/laser side and linear/square at the distal/skin side). There may also be different numbers of fibers in the excitation and collection optics; for example, the collection optics may include more fibers and/or fibers that support more modes for collecting more Raman light.

The bottom rows of FIG. 1B and FIG. 1E show that the linear arrays of fibers 116 and 126 in the excitation and collection probes 114 and 120, respectively, are positioned at the sides of the square metal ferrules 118 and 128. Positioning the fibers 116, 126 near the sides of the ferrules 118, 128 allows the fibers to address first and second spots 113, 123 that are closer together—in other words, with the smallest possible spatial offset A. The minimum offset between the pair of probes shown in FIGS. 1D and 1E was determined by the dimensions of the square ferrules and was 0.5 mm, or twice the distance from the edge of each square ferrule to the centers of the fibers.

FIG. 1C shows how the spatial offset A between the excitation probe 114 and the collection probe 120 can be varied to stimulate and collect Raman emissions 121 different layers of tissue and different locations within those layers. Keeping the probes close together, e.g., with the excitation probe 114 at the first spot 113 and the collection probe at a second spot 123a separated from the first spot 113 at a spatial offset A just greater than 0.5 mm (e.g., about 1.0 mm), leads to generation and collection of Raman light 121 from the layer of skin 11. Increasing the spatial offset to between 0.5 mm and 20 mm, e.g., by keeping the excitation probe 114 at the first spot 113 and moving the collection probe to a third spot 123b, leads to generation and collection of Raman light 121 from the layer of fat 13. (The spatial offset can also be increased by moving both probes 114, 120 or by moving the excitation probe 114 without moving the collection probe 120.) Increasing the spatial offset to more than 20 mm, e.g., by moving the collection probe to a fourth spot 123c, leads to generation and collection of Raman light 121 from the layer of muscle 15.

The spectrum and amplitude of the collected Raman light 121 depend on the type of tissue that produces the Raman light 121 because skin, fat, and muscle produce Raman peaks at different wavelengths and with different shapes and relative amplitudes. By monitoring the Raman spectrum as a function of the spatial offset, it is possible to estimate the thickness and composition of the fat layer 13: peaks associated with fat begin appearing at a smaller spatial offset (e.g., about 0.5 mm), indicating the thickness of the skin 11, and disappear at a larger spatial offset (e.g., about 15-20 mm), indicating the thickness of the fat 13. The relationship between the spatial offset and the fat depth/thickness depends on skin properties, such as scattering and absorption. The Raman signal also depends on the Raman cross section of the tissue, with fat having the largest Raman cross section among tissue constituents. The locations, shapes, and relative amplitudes of the peaks themselves reflect the composition of the fat layer 13. Thus, monitoring changes in the Raman spectrum as a function of the spatial offset or distance between the probe fibers provides a non-invasive measurement of fat thickness and composition. By measure repeatedly from same skin location, it is possible to track changes in relative fat thickness and composition over time.

FIGS. 1F and 1G illustrate the ferrule 118 and laser line filter 119 of the excitation probe 114 in greater detail. FIG. 1F shows a side view, with sample dimensions, and FIG. 1G shows an exploded end view, again with sample dimensions. In this example, the length of the fiber array is about 4.66 mm, the fiber core size is 200 µm, and the fiber's numerical aperture (NA) is 0.22. This yields an illumination area 117 illuminated by the laser light passing through the filter 119 that is about as 1.579 mm in width and 6.239 mm in length, or about 9.851 mm$^2$, if the filter 119 is pressed up against the skin 11.

The illumination area 117 and laser power level set the power density of Raman pump beam 111 on the skin 11. By IEC 60825, the damage threshold of 830 nm laser light for human skin is $2.6348 \times 10^4$ J/m$^2$. At a Raman pump power level of 200 mW, the optical power density is $2.030 \times 10^3$ J/m$^2$ for the probe 114 and illumination area 117 in FIGS. 1F and 1G. This is high enough to produce a detectable Raman emission 121 and well below the damage threshold for human skin.

A Portable SORS System for Subcutaneous Fat Measurement

FIG. 2 illustrates a portable, combined excitation and collection probe 200 for subcutaneous fat measurements in humans, swine, and other mammals. The combined excitation and collection probe 200 can be used with the laser 110, spectrometer 124, and processor 130 in FIG. 1A in place of the separate excitation probe 114 and collection probe 120. It can be used to measure Raman emissions from three different spatial offsets, and hence three different depths within the tissue, at the same time.

The probe 200 includes an input ferrule 210 that can be coupled to a Raman pump laser, such as a laser diode that emits Raman pump light at a wavelength of 830 nm. The input ferrule 210 includes one or more input/excitation fibers 212 with proximal or laser-side ends arranged in a circular array 216. These fibers 212 guide Raman pump light emitted by the laser to a head or ferrule 210 with a surface that can be placed against a subject's skin for in situ measurements. The excitation fibers 212 terminate in a linear array 216 on this surface and can be used to illuminate a line or array of spots on a subject's skin with Raman pump light.

This linear array 216 of excitation fibers 212 is parallel to several linear arrays 218a-218c of collection fibers 222 that collect at least a portion of the Raman light emitted by the tissue in response to the Raman pump light. These linear collection arrays 218a-218c are offset or separated from the linear excitation array 216 by distances of 1 mm, 5 mm, and 10 mm, enable the head 210 to measure Raman emission from several spots or patches on the subject's skin at the same time. (Other spatial offsets are also possible.) These offset locations can be optimized depending on the subject's skin color, obesity, or age. The collection arrays 218 can be fixed or moveable relative to each other and/or to the excitation fiber array 216 using a micrometer or by providing cassettes with different fiber holes for different spatial offsets.

The fibers 222 guide Raman emission light collected by the linear collection arrays 218a-218c to an output ferrule 224 that connects to a spectrometer, imaging spectrograph, or other suitable detector (not shown). In this example, the collection fibers 222 terminate in a single linear array with three sections or segments 226a-226c, each of which maps to a corresponding linear collection array 218a-218c. Rearranging the fibers in this manner makes it simpler to disperse the Raman emission in a single dimension, orthogonal to the linear array segments 226, with a grating, prism, or other dispersive element in the spectrometer. The proximal ends of the collection fibers 222 can also couple directly to passband/photodetector combinations for monitoring discrete spectral bins as discussed above. Alternatively, there can be at least two distal collection fiber arrays for each position, each of which is coupled to a reference bandpass filter (e.g., centered at 450 $cm^{-1}$) or a fat bandpass filter (e.g., centered at 1450 $cm^{-1}$) at its distal end and to a corresponding photodetector at its proximal end.

The excitation and collection fibers can be arrayed in other arrangements or shapes on the skin-contacting side of the head 210. For instance, the collection fibers can be arranged in a square or rectangular array that extends over a large portion or substantially the entire surface of the head 210. They could also be arranged concentrically in one or more annular arrays about a circular array of excitation fibers. Or they could be arranged in parallel linear arrays on both sides of a linear or rectangular array of excitation fibers. Similarly, there may be fewer (e.g., two) or more (e.g., four, five, or six) arrays of collection fibers, each at a different distance or spatial offset from the excitation array. These spatial offsets may be any value between about 0.5 mm and about 20 mm (e.g., 1, 2, 3, 4, 5, 10, 15, or 20 mm) and can be selected based on the expected depth and thickness of the fat layer.

Experimental Subcutaneous Fat Measurements

The system shown in FIGS. 1A-1G was used to measure the thickness and composition of subcutaneous fat in several pieces of pork. Pig skin is widely used as a model system for human skin. The structure and composition of pig skin are similar to the structure and composition of human skin, although the fat layer in pigs is usually thicker than fat layer in humans.

The system used light from an 830 nm diode laser (e.g., Process Instrument, Salt Lake City, USA) with a maximum output of 500 mW. This Raman excitation light was transmitted through the excitation probe, forming a linear illumination pattern on the sample tissue's surface to reduce photodamage. The incident power of the excitation laser was maintained at 200 mW at end face of the excitation probe. The power density at the surface of pork skin was $2.030 \times 10^3$ $J/m^2$ as calculated above. Raman signals were collected via the collection probe and were transferred to an imaging spectrograph (e.g., Holospec 1.8i, Kaiser Optical Systems, Michigan, USA) equipped with a charge-coupled device (CCD; e.g., PIXIS 256BR, Princeton Instruments, Massachusetts, USA). The spectrograph was installed with an additional notch filter to reduce the intensity of the reflected laser light. During the experiment, the pork pieces were placed on a quartz plate on a two-dimensional (2D) translational stage, with the truncated section facing the pair of fiber-optic probes horizontally. The collection probe could be displaced from the excitation probe vertically or horizontally to the truncated section up to 20 mm.

The animal tissue (i.e., the pork) used in this study was purchased from a grocery store. The samples were stored in a refrigerator at −18° C. to prevent sample deformation. The structure of the butchered pork, shown in FIG. 1C, was generally composed of skin, subcutaneous fat, and muscle layers. Also, the inter- and intramuscular fat layers were contained in the muscle layer.

The measurement was performed according to the fiber-optic-based SORS measurement method for estimating the subcutaneous fat thickness illustrated in FIG. 1C and described above. In this case, the tissue comprised pork chunks comprised primarily of skin, fat, and muscle layers arranged as in FIG. 1C. The excitation probe was positioned on the surface of each pork chunk and used to illuminate a linear section or patch of skin with laser light at a wavelength of 830 nm. The collection probe was initially located beside the excitation probe, and the distance between the centers of the probes (i.e., the spatial offset) was adjusted using a micrometer-controlled stage with a maximum travel range of 25 mm. Incident Raman photons penetrated pork tissue sample through a series of scattering events and were displaced from the entry point; thus, subsequent Raman scattering events occurred in the deep layer at a horizontally displaced position. As a result, Raman photons could be collected from the deep layer by displacing the collection probe farther from the excitation probe as shown in FIG. 1C.

FIGS. 3A-3F illustrate Raman spectroscopy conducted on the pure components (i.e., fat and muscle) with the SORS fiber-optic probe shown in FIGS. 1A-1G. For these measurements, the spatial offset was adjusted to the minimum value of 0.5 mm using the probe in FIG. 1B. The minimum offset was determined by measuring the distance between the surface of square metal ferrules. The subcutaneous fat content can be measured by monitoring the variation of Raman fat signal ($I_{fat}$) with respect to the spatial offset as discussed above and below.

FIG. 3A shows photographs of a model system with a well-defined fat thickness for testing the variation of the Raman fat signal as a function of the spatial offset. This model system was composed of three controlled fat thickness samples prepared by layering pork skin (top), fat (middle) layers of various thicknesses, and an extremely thick muscle layer. Fat tissue obtained from a pork chunk sample was cut into rectangular parallelepiped pieces. The skin-fat layers were 10/16/20 mm thick and layered on top of the muscle layer. In FIG. 3A, the top layer, which included both skin and fat components, was the same in all cases to ensure that the thickness of the skin remained constant. However, there was no middle layer (i.e., no additional fat layer) for 10 mm layer chunk shown at left in FIG. 3A.

FIG. 3B shows Raman spectra that are typical for biological fat and muscle samples. Fat tissue includes adipocytes, also known as fat cells, which contain a large number of lipid droplets. And muscle tissue is mainly composed of protein filaments, such as actin and myosin. Thus, the characteristic Raman spectra of the fat and muscle layers seen here originated from the lipid and protein components. In FIG. 3B, the difference between the Raman spectra of the fat and muscle layers was reflected in the broad band seen near 1300 $cm^{-1}$. The band of fat tissue produced Raman peaks at 1240 $cm^{-1}$ and 1300 $cm^{-1}$ corresponding to the =CH deformation and $CH_2$ twisting modes, respectively. Similar bands for the skin and muscle tissue samples were composed of amide III vibrations from the β-sheet and the α-helix.

The relative intensities of the respective bands varied depending on the composition of the biological tissue being analyzed. For the fat tissue samples shown in FIG. 3B, the intensity of the peak at 1300 cm$^{-1}$ was twice that of the peak at 1240 cm$^{-1}$. The intensity ratio of amide III vibrations (I1300/I1240) in muscle samples decreased, a trend which was characteristic of skin (muscle) tissue samples primarily composed of collagen (actin and myosin). Without being bound to a particular theory, this suggests that the contribution from the fat layer was higher than that of the skin (muscle) layer with increasing spatial offset.

FIGS. 3C and 3D show relative and normalized line-illuminated SORS spectra at different spatial offsets. In FIG. 3C, the spatial offsets range from 0.5 mm (top trace) to 6.5 mm (bottom trace) in 1 mm increments. In FIG. 3D, the spatial offsets range from 1.0 mm (bottom trace) to 7.0 mm (top trace) in 1 mm increments. FIG. 3C shows that the Raman intensity decreased considerably with increased distance between the excitation and the collection lines due to the decline in the excitation photon density.

In FIG. 3D, the standard normal variate (SNV)-corrected SORS spectra highlight the change observed in the Raman signature of the sample for increased offset. The Raman peaks of the fat samples were expected to increase with an ascending offset value due to the prevalence of the Raman photons emitted from the deep regions of the dissected meat sample. The major peaks in FIG. 3D are the typical Raman signatures observed for fatty acids. The peak in the dotted box at right was centered at about 1450 cm$^{-1}$ and was representative of fatty acids, whereas the peak in the solid box at left was centered at about 450 cm$^{-1}$ and was representative of a reference since it remained the same during the experiment. The most significant contribution to the reference band came from the Raman background from the silica core of optical fiber that guided the Raman pump beam to the sample, suggesting that the Raman intensity of the reference band was independent of the fluctuations noted in the tissue samples' constituents. Accordingly, the integrated band intensity of this band was set to $I_{Ref}$.

FIG. 3E is a plot of the Raman intensity ratio, which is defined as the normalized Raman intensity of the fatty acid ($I_{Fat}/I_{Ref}$), versus spatial offset, where $I_{Fat}$ is the area under the fat peak centered at about 1450 cm$^{-1}$ (in the dotted box in FIG. 3D) and $I_{Ref}$ is the area under the reference peak at about 450 cm$^{-1}$. These areas can be computed by integrating under each peak for about ±25 cm$^{-1}$ in from the peak center wavelengths, though it is not necessary to integrate over the same bandwidth for each peak (e.g., the integral for the fat peak can extend for 50 cm$^{-1}$ and the integral for the reference peak can extend for 45 cm$^{-1}$).

The Raman intensity ratio is a parameter for correlating the Raman spectra to the fat thickness. Even for small offset values, the SORS readings contained blended spectra, which were obtained from both skin and subcutaneous fat samples because the skin layer was very thin. A significant increase was noted in both the offset and the $I_{Fat}/I_{Ref}$ values due to the prevalence of deep Raman signals, as is typical for SORS experiments. The ascending $I_{Fat}/I_{Ref}$ slope was proportional to the fat thickness of each model. The increment of each plot becomes small for large offset values in the figure. As the thick muscle layer is placed under the fat, the SORS signals do not change significantly at large offset. The vertical offset of each plot was derived from the position at which the readings were conducted during the experiment. This issue was eliminated by setting all vertical offsets to zero.

FIG. 3F illustrates the adjusted $I_{Fat}/I_{Ref}$ ratio (i.e., the adjusted Raman intensity ratio). The adjusted Raman intensity ratio in FIG. 3F is the Raman intensity ratio in FIG. 3E scaled so that the values for the spatial offset of 0.5 mm coincide at 0. FIG. 3F shows that the slope of the adjusted Raman intensity ratio rose sharply when the thickness of the respective fat layer was increased.

The fat models shown in FIG. 3A included three components: skin, fat, and muscle layers. Since each model has the same top (skin) layer, the Raman contribution from the skin layer should have been the same for all cases. But this did not account for the differences seen in the ascending slope. The fat signal increased due to the presence of a thick layer of fat tissue. The bottom layer, which was a piece of meat (muscle) sample, had a small Raman scattering cross-section, thus, making it difficult for photons to penetrate and leading to diminishing Raman signals from the nearby fat layer. This attenuation resulted in the gradually sloping Raman signal attributed to the fat layer.

FIGS. 4A-4C illustrate correlation of the fat thickness and the Raman intensity ratio. FIG. 4A shows a pork chunk chopped into five pieces, shown from various angles. Although the fat composition of each piece was complex, the overall fat content of the pork chunk decreased as seen from left to right in the respective photographs. FIG. 4B shows the adjusted Raman intensity ratio for these pork pieces plotted against the spatial offsets. As in the three-layer plots in FIGS. 3E and 3F, the slope of the Raman intensity ratio decreased relative to the apparent thickness of the chopped chunks. FIG. 4C is a bar chart showing the slope versus thickness for the different pork chunks. The results were quantified by calculating the slope of the Raman intensity ratio with a linear regression, and the resulting correlation between the apparent thickness and the Raman slope is presented in FIG. 4C. The correlation in FIG. 4C indicates that the fat constitution of the meat sample could be estimated from the Raman spectra.

FIGS. 5A-5C illustrate SORS and OLS regression analyses. Once the analyses were completed, the pork chunks were chopped into nine smaller pieces, labeled 1-9 in FIG. 5A, and examined. In this case, the fat thickness decreased, as seen in the photograph in the direction from left to right. The slope of the Raman intensity also decreased from left to right (from sections 1 to 9). FIG. 5B shows the adjusted Raman intensity ratio as a function of the spatial offsets that at the nine different positions in FIG. 5A. The values obtained for the slope were proportional to the apparent fat thickness seen in the photographs.

Elucidating the composition of the pork tissue was undertaken via OLS regression for the SORS spectra of all nine sections. OLS regression can deconstruct a complex spectrum into its spectral components. Here, OLS regression was applied to determine the tissue composition of the pork sample pieces relative to their respective depth from the skin layer. For simplicity, it was assumed that the pork tissue samples consisted of fat and muscle layers only. For the OLS simulation, two basis spectra were acquired as the explanatory variables, and the fat and nonfat components were assigned as arbitrary units. The two basis spectra were measured for the pure fat and the muscle layer (major nonfat) components. During optimization, the sum of the squares of the differences between the SORS spectra and the linear sum of the two explanatory variables were minimized, thereby giving information about the content of the respective tissue components.

FIG. 5C shows OLS plots for the different sections of pork labeled in FIG. 5A. The filled circles and squares in the plots correspond to the content of fat and nonfat (muscle) tissue, respectively, and the sum of these two components was taken to be 100%. The abundance of each component did not automatically represent the quantity; rather, it was proportional to the volume of each component. The content of the bicomponent at the minimum offset was similar for all sections, as shown in FIG. 5C. However, the fluctuations observed were of physical importance.

The OLS plot in FIG. 5C for Section 1 (upper left) shows that the relative abundance of the fatty tissue increased abruptly as a function of the spatial offset for the "thick fat" tissue. On the contrary, the nonfat content (muscle) increased steadily for the "thin fat" tissue samples. The Raman spectra of the skin layers were not vastly different from those obtained for the muscle layers when both were compared to the fat layers. This observation could be attributed to the scattering of incident photons upon penetration of the skin layers because the outermost portions of the skin layers were composed chiefly of collagen fibrils. For thick fat layers, the Raman signals from the skin decreased with an accompanying increase in the Raman signals emitted from the fat layer. For thin fat layers, the Raman signals emitted from the skin layers decreased for smaller offsets and remained constant with larger offsets. The relative abundance of the nonfat component could be regarded as contributions of both the skin and the muscle layers. Thus, the spectra of the muscle layers in the "thin fat" chunks compensated for the reduced spectra observed for the skin (top) layers, and their sums remained relatively unchanged, as shown in the OLS plot of sections 6 to 9 (bottom row). Consequently, the photograph in FIG. 5A and the nine OLS plots in FIG. 5C indicate that the apparent thickness was closely related to the variations observed for the calculated OLS values. The relative abundance of fat increased according to the spatial offset associated with various rising slopes that were proportional to the thickness of the fat layer. FIG. 5D is a plot of the slope of the adjusted Raman intensity ratio versus apparent fat thickness for each of the sections. The inset at upper left shows the high correlation between the slope of the adjusted Raman intensity ratio versus apparent fat thickness.

Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain, using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of," or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of measuring a subcutaneous fat layer in a mammal, the method comprising:
    illuminating a first spot on the skin of the mammal with a Raman pump beam, the Raman pump beam exciting a Raman emission from the subcutaneous fat layer;
    detecting the Raman emission at a second spot on the skin of the mammal that is spatially offset from the first spot on the skin of the mammal; and
    estimating a thickness of the subcutaneous fat layer based on the Raman emission and a distance between the first spot and the second spot.

2. The method of claim 1, wherein the distance between the first spot and the second spot is 0.5 mm to 20.0 mm.

3. The method of claim 1, wherein the Raman emission is a first Raman emission, and further comprising:
    detecting a second Raman emission at a third spot on the skin of the mammal that is spatially offset from the first spot on the skin of the mammal and from the second spot on the skin of the mammal, and
    wherein estimating the thickness of the subcutaneous fat layer is further based on a distance between the first spot and the third spot and the second Raman emission.

4. The method of claim 3, wherein estimating the thickness of the subcutaneous fat layer comprises:
    determining Raman intensity ratios for the second spot and the third spot based on peaks in Raman spectra of the first Raman emission and the second Raman emission; and
    estimating a variation of the Raman intensity ratio with distance from the first spot based on the Raman intensity ratios.

5. The method of claim 4, wherein determining the Raman intensity ratios comprises determining an area under a peak associated with the subcutaneous fat layer.

6. The method of claim 5, wherein determining the Raman intensity ratios further comprises determining an area under a reference peak.

7. The method of claim 6, wherein the reference peak is at about 450 cm$^{-1}$ and the peak associated with the subcutaneous fat layer is at about 1450 cm$^{-1}$.

8. The method of claim 7, wherein estimating the thickness of the subcutaneous fat layer comprises determining a slope of the variation of the Raman intensity ratio with distance from the first spots.

9. A system for measuring a subcutaneous fat layer in a mammal, the system comprising:
    a laser to emit a Raman pump beam;
    excitation optical fibers, in optical communication with the laser and having distal ends arranged in a first array, to guide the Raman pump beam to a first spot on the skin of the mammal, the Raman pump beam exciting a Raman emission from the subcutaneous fat layer;
    collection optical fibers, having distal ends arranged in a second array, to detect the Raman emission at a second spot on the skin of the mammal;
    a detector, in optical communication with the collection optical fibers, to measure a variation in amplitude of a spectral component of the Raman emission associated with the subcutaneous fat layer; and
    a processor, operably coupled to the detector, to estimate a thickness of the subcutaneous fat layer based on the variation in amplitude of the spectral component and a distance between the first spot and the second spot.

10. The system of claim 9, wherein the detector comprises a spectrometer.

11. The system of claim 9, wherein the detector comprises:
    a first bandpass filter, having a passband centered at about 450 cm$^{-1}$, to transmit a reference spectral component of the Raman emission;
    a first photodetector, in optical communication with the first bandpass filter, to detect the reference spectral component of the Raman emission;
    a second bandpass filter, having a passband centered at about 1450 cm$^{-1}$, to transmit a fat spectral component of the Raman emission; and
    a second photodetector, in optical communication with the second bandpass filter, to detect the fat spectral component of the Raman emission.

12. The system of claim 9, wherein the processor is configured to estimate the thickness of the subcutaneous fat layer by:
    determining Raman intensity ratios for the second spot and the third spot based on peaks in Raman spectra of the first Raman emission and the second Raman emission; and
    estimating a variation of the Raman intensity ratio with distance from the first spot based on the Raman intensity ratios.

13. The system of claim 12, wherein determining the Raman intensity ratios comprises determining an area under a peak associated with the subcutaneous fat layer at about 1450 cm$^{-1}$.

14. The method of claim 13, wherein determining the Raman intensity ratios further comprises determining an area under a reference peak at about 450 cm$^{-1}$.

15. The system of claim 14, wherein estimating the thickness of the subcutaneous fat layer comprises determining a slope of the variation of the Raman intensity ratio with distance from the first spots.

16. The system of claim 9, further comprising:
    a first ferrule to hold the distal ends of the excitation optical fibers against the skin of the mammal at the first spot; and
    a second ferrule, moveable with respect to the first ferrule, to hold the distal ends of the collection optical fibers against the skin of the mammal at the second spot.

17. The system of claim 9, further comprising:
    a ferrule to hold the distal ends of the excitation optical fibers against the skin of the mammal at the first spot and to hold the distal ends of the collection optical fibers against the skin of the mammal at the second spot.

18. The system of claim 17, wherein the distance between the first spot and the second spot is a first distance, and further comprising:
- additional collection optical fibers, having distal ends arranged in a third array and held in place by the ferrule, to detect the Raman emission at a third spot on the skin of the mammal, the third spot separated from the first spot by a second distance greater than the first distance.

19. The system of claim 18, wherein the first distance is between 0.5 mm and 5 mm and the second distance is between 5 mm and 20 mm.

20. A method of measuring a subcutaneous fat layer in a mammal, the method comprising:
- illuminating a first spot on the skin of the mammal with a Raman pump beam, the Raman pump beam exciting a Raman emission from the subcutaneous fat layer;
- measuring a variation in amplitude of a spectral component of the Raman emission associated with the subcutaneous fat layer as a function of distance from the first spot; and
- estimating a thickness of the subcutaneous fat layer based on the variation in amplitude of the spectral component.

21. The method of claim 20, further comprising:
- estimating a composition of the subcutaneous fat layer based on the amplitude of the spectral component.

\* \* \* \* \*